United States Patent [19]

Mills et al.

[11] Patent Number: 4,796,641

[45] Date of Patent: Jan. 10, 1989

[54] DEVICE AND METHOD FOR CHRONIC IN-VIVO MEASUREMENT OF INTERNAL BODY PRESSURE

[75] Inventors: Perry A. Mills, Roseville; Brian P. Brockway, Minneapolis, both of Minn.

[73] Assignee: Data Sciences, Inc., Minneapolis, Minn.

[21] Appl. No.: 69,728

[22] Filed: Jul. 6, 1987

[51] Int. Cl.⁴ .............................................. A61B 5/00

[52] U.S. Cl. .................................... 128/748; 128/673; 128/903; 128/DIG. 13; 604/892.1; 604/247

[58] Field of Search .................... 128/672.5, 748, 903, 128/DIGS. 12–13; 604/246–247, 266, 892.1

[56] References Cited

U.S. PATENT DOCUMENTS

| | | | |
|---|---|---|---|
| 3,663,288 | 5/1972 | Miller | 604/266 |
| 4,114,603 | 9/1978 | Wilkinson | 128/748 |
| 4,127,110 | 11/1978 | Bullara | 128/903 X |
| 4,373,527 | 2/1983 | Fischell | 128/903 X |
| 4,443,218 | 4/1984 | DeCant, Jr. et al. | 128/DIG. 13 X |
| 4,509,946 | 4/1985 | McFarlane | 604/246 |
| 4,540,027 | 9/1985 | Forberg | 604/247 X |
| 4,608,996 | 9/1986 | Brown | 128/748 X |
| 4,626,244 | 12/1986 | Reinicke | 604/892.1 X |

FOREIGN PATENT DOCUMENTS

| | | | |
|---|---|---|---|
| 3207044 | 10/1983 | Fed. Rep. of Germany | 128/673 |
| 2459036 | 2/1981 | France | 128/903 |

OTHER PUBLICATIONS

Latimer et al., "Continuous Flushing Systems", *Anesthesia*, vol. 29, 1974, pp. 307–317.
L. S. Watson, et al., "Continuous Recording of Arterial Blood Pressure in Conscious Rats", *New Antihypertensive Drugs*, 1976, pp. 87–96.
P. M. Hutchins, et al., "Acute and Chronic Measurement of Arterial Pressure in the Rat", Bowman Gray School of Medicine, pp. 33–40.
Bernward Garthoff, et al., "A New System for the Continuous Direct Recording of Blood Pressure and Heart Rate in the Conscious Rat", *Journal of Pharmacological Methods*, 1981, pp. 275–278.
James R. Weeks, et al., "Routine Direct Measurement of Arterial Pressire in Unanesthetized Rats", pp. 646–648.
Ruben D. Bunag, "Facts and Fallacies About Measuring Blood Pressure in Rats", *Clin. and Exper. Hyper.-Theory and Practice*, 1983, pp. 1659–1681.
Miklos Gellai, et al., "Chronic Vascular Constrictions and Measurements of Renal Function in Conscious Rats", *Kidney International*, vol. 15 (1979), pp. 419–426.
Konigsberg Instruments, Inc., "Implantable Pressure Transducers for Animal Research", brochure 06/01/82-Rev A.
Konigsberg Instruments, Inc., "One and Two Channel Telemetry Systems" (brochure), 4 pages.
Konigsberg Instruments, Inc., "Multichannel Telemetry Systems", 4-page brochure.
Kenneth J. Dormer, "Transducer Implantation", Reprinted from *Medical Electronics*, Oct. 1980, pp. 69–75.
Robert J. Gronan, et al., "Routine, Direct Measurement of Aortic Pressure in the Conscious Rabbit", *Physiology & Behavior*, vol. 30, pp. 719–722, 1983.
Thomas A. Patrick, et al., "Telemetry of Left Ventricular Diameter and Pressure Measurements from Unrestrained Animals", *Journal of Applied Physiology*, Aug. 1974, pp. 276–281.
W. H. Ko, et al., "Intracranial Pressure Telemetry System" *Bioteletry Patient Monitg*, 1981, pp. 131–150.
Albert M. Leung, et al., "Intracranial Pressure Telemetry System Using Semicustom Integrated Circuits, *IEEE Transactions on Biomedical Engineering*", Apr. 1986, pp. 386–395.
W. A. Mann, et al., "A Simple Procedure for Direct Blood Pressure Measurements in Conscious Dogs", *Laboratory Animal Science*, 1986, 8 pages (Reprint).

*Primary Examiner*—Kyle L. Howell
*Assistant Examiner*—Angela D. Sykes
*Attorney, Agent, or Firm*—Kinney & Lange

[57] ABSTRACT

A device capable of sensing pressure allows the sensor and amplifying electronics to be packaged in a very small size and implanted within the body. The sensor consists of a small catheter, the tip of which is placed at the point at which pressure is to be measured, attached to a solid-state pressure sensor. The catheter is filled with a fluid and is connected to an implantable infusion pump which dispenses through the lumen of the catheter, heparin or other drug which inhibits thrombogenisis.

11 Claims, 1 Drawing Sheet

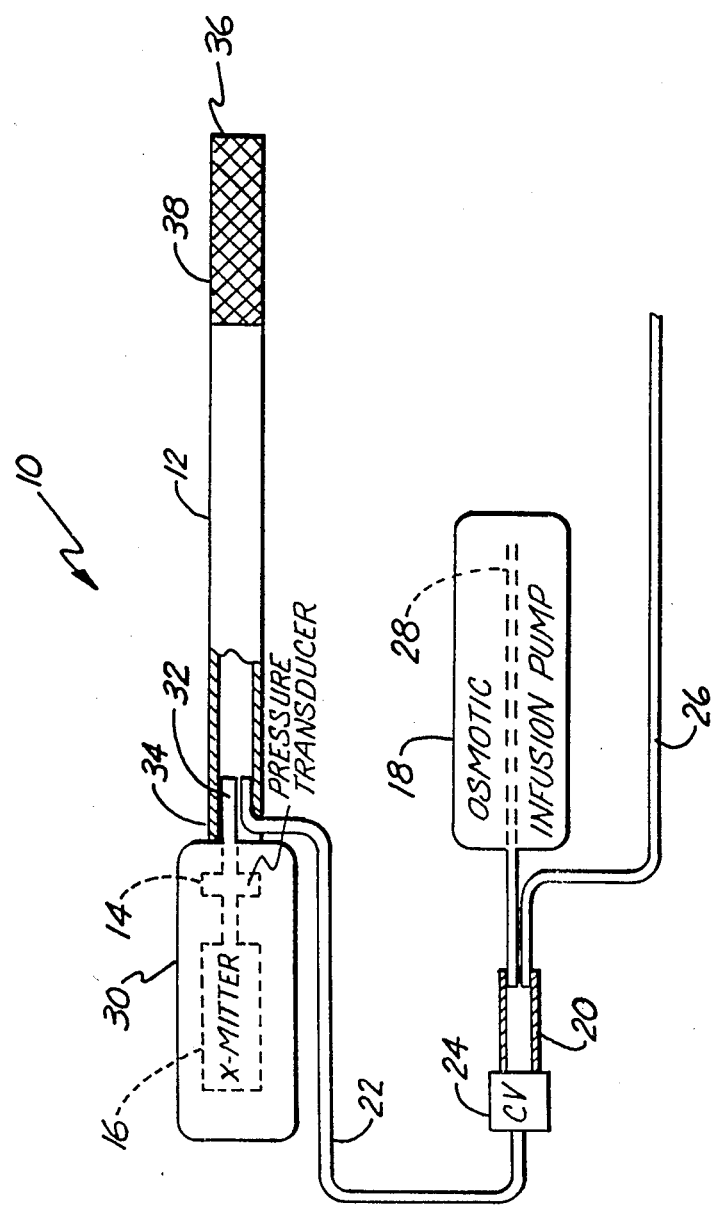

DEVICE AND METHOD FOR CHRONIC IN-VIVO MEASUREMENT OF INTERNAL BODY PRESSURE

BACKGROUND OF THE INVENTION

1. Field of the Invention

The present invention relates to a means of measuring physiological pressures, including blood pressure, intracranial pressure, intrapleural (for evaluation of respiratory function and respiration rate) pressure, pressure within the gastrointestinal system.

2. Description of the Prior Art

Laboratory animals are often used as models of human response to various stimuli and pharmacological agents. Such models are used to project the effect of pharmaceutical compounds, determine the toxicity of chemicals, and to better understand human physiology.

Ony physiological parameter of interest in such evaluations is blood pressure. In many cases, because blood pressure fluctuates with the time of day and is episodic, it is necessary to obtain chronic and frequently sampled measurement of blood pressure within a given animal in order to assess the effects of an agent over a time course. There are several methods which are currently used for chronic measurement of blood pressure. These include the tail cuf method, chronic cannulation, the use of implantable pressure sensors in combination with telemetry, and the use of a vascular access port.

The tail cuff method is well developed with several manufacturers producing such a device. In this case, the animal (usually a rat) is placed in a restraining device. An inflatable cuff is placed on the tail. A blood flow sensor (either plethysmographic or Doppler utrasound) is usually integral to the cuff. The cuff is inflated until blood flow has ceased and is then deflated. The first indication of pulsatile flow and the first indication of continuous flow are noted as the systolic and diastolic pressures, respectively. Some of these devices require that the arteries of the animal be dilated by heating the entire body of the animal to 40° C. or more, causing significant stress on the animal and subsequent artifact. Since these devices require that the animal be restrained, artifact is introduced due to the stress of handling and restraint. In addition, it is not possible to humanely obtain measurements from an animal at frequent intervals with this method, and it is very labor intensive.

Chronic cannulation is the most frequently used method for measurement of blood pressure. With this method, a small catheter is inserted into an artery, typically and carotid, descending abdominal aorta, or femoral artery. The catheter is exteriorized at a point, typically on the back, which generally prevents it from being destroyed by the animal. The catheters from a number of animals may be connected to a single pressure transducer through solenoid valves. A pump is typically used with each animal to continuously backflush the catheter with a heparinized saline or other anticoagulant solution. In addition, a swivel must be used on each catheter to prevent it from becoming tangled as the animal moves about the cage. The solenoid valves and pressure transducers are often connected to a computer to allow frequent sampling of pressure from each animal. This method has several disadvantages: First, since the catheter is long and relatively small in diameter, the higher frequency components of the pressure waveform are lost. Second, even though precautions are taken, the animals often become tangled in the catheter or learn to grab the catheter with their teeth or paws, and subsequently bleed to death. Third, keeping the catheters patent requires considerable maintainance and is thus labor intensive.

Implantable pressure sensors are sometimes used in combination with telemetry. This eliminates some of the disadvantages pointed about above. Konigsburg Instruments manufactures a sensor which is 3.5 mm in diameter. However, this sensor is too large for many applications, and since it is most frequently necessary to mount it in the wall of a vessel, it is subject to fibrous tissue growth over the sensing diaphragm which results in drift of the measured signal. In addition, the nature of the transducer is such that drift is inherent and requires frequent in-vivo calibration.

Miniature solid state sensors mounted on the tip of a catheter have also been used to measure internal body pressures. Some commercially available devices are as small as 1 mm diameter. Because of the inherent instability of these devices they require calibration within a short time prior to use and are suitable only for acute measurements.

In larger animals (dogs, etc.), it is possible to implant a vascular access port in the femoral artery. In this approach, a catheter is attached to a reservoir opposite a diaphragm. The diaphragm can be pierced with a needle connected to a pressure transducer when acquiring pressure measurements and flushing the catheter. The disadvantage of this approach is that it is labor intensive. A sterile protocol is required each time the diaphragm is pierced. In addition, the catheter requires bi-weekly flushing in order to maintain patentcy. If sterile protocol is broken, the animal may develop infection, requiring expensive antibiotics and removal from the study until the infection clears.

SUMMARY OF THE INVENTION

The present invention is an implantable pressure sensing device which includes an implantable catheter means, implantable pressure sensing means, and implantable osmotic infusion pump means. The catheter means has its distal end placed at a position within the animal at which an internal body pressure (such a blood pressure) is to be sensed. The pressure sensing means is connected to the proximal end of the catheter, and provides a signal which is a function of the internal body pressure. In preferred embodiments, the pressure sensing means includes a pressure transducer and a transmitter for transmitting a signal out of the animal as a function of the sensed pressure. The osmotic infusion pump means is connected to the proximal end of the catheter means and supplies doses of an antithrombogenic solution through the catheter means to the distal end to prevent or reduce clotting which would prevent pressure from being sensed.

BRIEF DESCRIPTION OF THE DRAWINGS

The FIGURE shows a preferred embodiment of the implantable pressure sensing device of the present invention.

DETAILED DESCRIPTION OF THE PREFERRED EMBODIMENTS

Pressure measurement device 10 shown in the FIGURE is a very small, lightweight device which can be implanted into small animals, such as rats, to provide chronic measurement of internal body pressures such as blood pressure. Device 10 includes pressure sensing catheter 12, pressure transducer 14, transmitter 16, osmotic infusion pump 18, catheters 20 and 22, check valve 24, access catheter 26, and flow restrictor 28.

As shown in the FIGURE, transducer 14 and transmitter 16 are contained within housing 30. Nipple 32 at one end of housing 30 communicates with pressure transducer 14 and is inserted into proximal end 34 of catheter 12. Distal end 36 of catheter 12 is inserted, for example, in an artery of an animal to transmit pressure of fluid within that artery back to pressure transducer 14 within housing 30. The sensed pressure is converted to electrical signals by transmitter 16, and a telemetry signal is transmitted to an external receiver (not shown).

Catheter 12 is a small diameter, hollow tube made of a biocompatible material such as urethane. Patentcy of catheter 12 is maintained with very low doses of a drug (in many cases a subsystemic dose). The drug (which is an antithrombogenic solution) is supplied by implantable osmotic infusion pump 18 through tube 20, check valve 24, and catheter 22 to proximal end 34 of catheter 12. In the preferred embodiment shown in the FIGURE, the end of catheter 22 is welded in side-by-side relationship to nipple 32, and proximal end 34 of catheter 12 slips over and is connected to both catheter 22 and nipple 32.

The ability to maintain catheter patentcy at low doses of antithrombogenics is due to a very low system compliance for device 10 which prevents blood from entering catheter 12 in the presence of fluctuating pressures. In addition, film coating 38 (shown as cross-hatched in the FIGURE) is formed on the distal end 36 of catheter 12. Film coating 38, which is preferably a urethane coating, provides a smooth surface which reduces the ability of thrombi to adhere to catheter 12 in the presence of arterial blood flow. In addition, coating 38 rounds over the distal end of catheter 36, and provides a flow profile which reduces the presence of eddy currents at the distal tip of catheter 12. The stable interface of heparinized saline (or other antithrombogenic drug) exiting the lumen of catheter 12 at distal end 36 provides a constant diffusion of the drug at the distal tip, where it is most needed.

Low system compliance is achieved by the use of catheter materials for catheters 12, 20 and 22 and dimensions of those catheters which provide the least compliance consistent with their intended purpose. For example, in a preferred embodiment of the present invention, catheter 12 is a urethane tube having approximately a 0.7 mm outside diameter and a 0.2 mm wall thickness. The use of urethane tubing, rather than more compliant silicon tubing, for example, together with the relatively thick wall minimizes compliance consistent with the need of catheter 12 to be inserted into an artery of a small animal such as a rat.

Catheters 20 and 22 do not require the same flexibility, because they are not inserted into an artery. In a preferred embodiment, catheters 20 and 22 are polyethylene or polyvinyl chloride tubes.

Flow restrictor 28, which in one embodiment is a 75 micron inside diameter glass-inside-stainless steel tube, reduces the compliance of osmotic fusion pump 18. This prevents blood from entering distal tip 36 of catheter 12 during diastole.

In addition, check valve 24 is connected in the flow path from osmotic infusion pump 18 to catheter 12. The purpose of check valve 24 is to prevent blood from entering catheter 12 due to pump 18 compliance when the mean blood pressure of the animal increases significantly.

Access catheter 26 is connected to catheter 20 in parallel with the outlet of infusion pump 18. Access catheter 26 extends out of the animal's body. Prior to placement of pump 18 within the animal's body, and prior to pump 18 reaching a satisfactory low level following implantation, fluid flow is provided from an external infusion pump (not shown) through access catheter 26, catheter 20, check valve 24, and catheter 22 to catheter 12.

After osmotic infusion pump 18 is operating, catheter access 26 can be closed by simply sticking a pin (not shown) in its outer end, which keeps fluid from leaking out of access catheter 26. By removing the pin and connecting an external pressure transducer to access catheter 26, a technician can monitor the pressure being sensed by catheter 12 and thus verify that pressure transducer 14 and transmitter 16 are operating properly. In addition, in the event that catheter 12 becomes blocked for some reason, access catheter 26 can be used to supply fluid at a pressure sufficient to flush out catheter 12, thus returning it to patentcy.

Device 10 of the present invention has been successfully used to monitor blood pressure in small animals such as rats by implanting all of device 10 within the body of the animal, except for the outer end of access catheter 26. In preferred embodiments, housing 30 is implanted and secured within the peritoneal cavity; distal end 36 of catheter 12 is placed in the descending aorta by inserting catheter 12 through the wall in the artery and fixing in place with either silk suture or tissue adhesive; and pump 18 (which is preferably an Alza osmotic infusion pump) is implanted above the neck of the animal. The placement of pump 18 provides reasonable access to permit replacement of the pump 18 as necessary.

In summary, the present invention offers significant advantages over prior art techniques for monitoring pressure in laboratory animals. With the present invention, pressure transducer 14 is placed remote from the vessel, with pressure being transmitted to transducer 14 through a fluid-filled catheter 12. This allows the capability of measuring pressure within a very small vessel with excellent long term stability because it allows the use of stable, commercially available sensors which cannot be packaged in a size which could allow direct insertion into the vessel of a small animal. Since the device also incorporates a means of reducing fibrous growth on the catheter, it is possible to reduce or eliminate the contribution of fibrotic growth to measurement instability. In addition, the use of implantable osmotic infusion pump 18 allows an antithrombogenic drug to be dispensed through the lumen of catheter 12 to maintain catheter patentcy. The use of osmotic infusion pump 18 allows nearly all of device 10 to be enclosed within the body of the animal.

Device 10 of the present invention (combined with a radiotelemetry receiver and computerized data collecting system) makes it is possible to automate the process of collection of pressure data from laboratory animals. This provides better quality and more frequent data while reducing the cost of implementing many experimental protocals. The present invention allows the animals to move freely within their cages, which not only reduces stress caused by tethers, but also provides a more humane treatment of the animal.

The device 10 of the present invention also is applicable to sensing internal body pressure in humans, including blood pressure, interplural pressure, intracranial pressure, and pressures within the gastointestinal system. Such information can be used for diagnostic purposes, or as feedback for closed loop control of infusion pumps capable of administering pharmaceutical agents.

Although the present invention has been described with reference to preferred embodiments, workers skilled in the art will recognize that changes may be made in form and detail without departing from the spirit and scope of the invention.

What is claimed is:

1. An inplantable device for sensing an internal body pressure of an animal, the device comprising:
   implantable catheter means having proximal and distal ends, the distal end for placement at a position within the animal at which the internal body pressure is to be sensed;
   implantable pressure sensing means connected to the proximal end of the catheter means for providing a signal which is a function of the internal body pressure;
   implantable osmotic infusion pump means connected to the proximal end of the catheter means for supplying doses of an antithrombogenic solution to the distal end; and
   means associated with the osmotic infusion pump means for preventing body fluid from entering the distal end of the catheter means.

2. The device of claim 1 wherein the means for preventing body fluid from entering the distal end includes flow restrictor means associated with the osmotic infusion pump means.

3. The device of claim 1 wherein the means for preventing body fluid from entering the distal end includes check valve means connected between the osmotic infusion pump means and the catheter means.

4. The device of claim 1 wherein the catheter means includes a coating on an outer surface at its distal end for reducing ability of thrombi to adhere to the distal end.

5. The device of claim 4 wherein the coating is a urethane material.

6. The device of claim 1 and further including:
   access catheter means connected to the proximal end for providing fluid flow through the catheter means during and following implantation prior to the osmotic infusion pump means reaching a desired output flow.

7. The device of claim 1 wherein the pressure sensing means includes:
   pressure transducer means connected to the proximal end for providing a transducer signal which varies as a function of the fluid pressure at the proximal end; and
   transmitter means connected to the transducer means for transmitting a signal out of the animal which is a function of the transducer signal.

8. The device of claim 7 wherein the pressure sensing means further includes:
   housing means for housing the pressure transducer means and the transmitter means.

9. A method of sensing an internal body pressure within a body of an animal, the method comprising:
   implanting within the body of the animal a sensing catheter with a distal end of the sensing catheter positioned to be exposed to the internal body pressure;
   implanting a pressure transducer within the body with a proximal end of the sensing cathêter for providing a transducer signal as a function of fluid pressure at the proximal end;
   implanting an osmotic infusion pump within the body and connected to the proximal end of the sensing catheter for supplying doses of an antithrombogenic solution through the sensing catheter to the distal end;
   implanting a transmitter within the body and connected to the pressure transducer for transmitting a transmitter signal out of the animal which is a function of the transducer signal; and
   monitoring the transmitter signal over an extended time period to provide a record of variation of the internal body pressure over time.

10. The method of claim 9 and further comprising:
    connecting a check valve in a flow path between the osmotic infusion pump and the sensing catheter to prevent body fluid from entering the distal end of the catheter.

11. The method of claim 9 and further comprising:
    connecting an access catheter to the proximal end of the sensing catheter with a proximal end of the access catheter being accessable from outside the body of the animal; and
    providing fluid flow through the access catheter to the sensing catheter during and following implantation until the osmotic infusion pump reaches a desired output fluid flow.

* * * * *